US006248985B1

(12) United States Patent
Tomasello

(10) Patent No.: US 6,248,985 B1
(45) Date of Patent: *Jun. 19, 2001

(54) APPARATUS AND METHOD FOR THE DISINFECTION OF MEDICAL WASTE IN A CONTINUOUS MANNER

(75) Inventor: Anthony J. Tomasello, Libertyville, IL (US)

(73) Assignee: Stericycle, Inc., Lake Forest, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/238,525

(22) Filed: Jan. 27, 1999

(30) Foreign Application Priority Data

Jun. 1, 1998 (BR) .................................... 9806362

(51) Int. Cl.⁷ ...................................... H05B 6/64
(52) U.S. Cl. .......................... 219/679; 219/770; 219/762; 219/775; 422/22; 241/606
(58) Field of Search ..................................... 219/679, 770, 219/775, 651, 774, 701, 710, 762, 700, 690; 422/22, 23, 21, 26, 287, 295; 241/606

(56) References Cited

U.S. PATENT DOCUMENTS

| 2,114,345 | 4/1938 | Hayford . |
| 2,486,684 | 11/1949 | Schlesman et al. . |
| 2,542,028 | 2/1951 | Hodge . |
| 2,564,579 | 8/1951 | Parmenter et al. . |
| 2,731,208 | 1/1956 | Dodd . |
| 2,897,365 | 7/1959 | Dewey et al. . |
| 2,958,570 | 11/1960 | Fessler . |

(List continued on next page.)

FOREIGN PATENT DOCUMENTS

| 3710156 | 10/1988 | (DE) . |
| 271454 | 9/1989 | (DE) . |
| 0098595 | 1/1984 | (EP) . |
| 2078203 | 11/1971 | (FR) . |
| 532502 | 1/1941 | (GB) . |

(List continued on next page.)

OTHER PUBLICATIONS

Chipley "Effects of Microwave Irradiation on Microorganisms." *Advances Applied Microbiology* vol. 26 (1980), pp. 129–145.

Bill Paul. "Combustion Says Firm Sterilizes Medical Waste With Microwaves." *The Wall Street Journal*, p. B3 (Apr. 10, 1989).

"Science Watch: Microwave Sterilizer is Developed." *New York Times;* (Jun. 20, 1989).

"Mechanism of Microwave Sterilization in the Dry State." Unknown source. Published prior to Jan. 27, 1999.

"Medical Waste Treatment by Microwave Technology", Norcal Solid Waste Systems. Published prior to Jan. 27, 1999.

Christensen et al. "The Multi–Purpose Irradiation Plant and the Quality Contol of Radiation Sterilization of Medical Equipment." Proceedings of the Fourth International Conference on the Peaceful Uses of Atomic Energy (held in 1971), vol. 14 (1972), pp. 345–354.

(List continued on next page.)

*Primary Examiner*—Tu Ba Hoang
(74) *Attorney, Agent, or Firm*—Brinks Hofer Gilson & Lione

(57) ABSTRACT

A method of processing medical waste which includes the steps of continuously feeding medical waste into a tube and heating the medical waste passing through the tube with electromagnetic radiation so as to heat and disinfect the medical waste.

16 Claims, 7 Drawing Sheets

U.S. PATENT DOCUMENTS

| | | |
|---|---|---|
| 3,095,359 | 6/1963 | Heller . |
| 3,215,539 | 11/1965 | Landy . |
| 3,261,140 | 7/1966 | Long et al. . |
| 3,329,796 | 7/1967 | Manwaring . |
| 3,387,378 | 6/1968 | Newsom . |
| 3,490,580 | 1/1970 | Brumfield et al. . |
| 3,494,723 | 2/1970 | Gray . |
| 3,494,724 | 2/1970 | Gray . |
| 3,547,577 | 12/1970 | Lovercheck . |
| 3,551,090 | 12/1970 | Brumfield et al. . |
| 3,589,276 | 6/1971 | Swallert . |
| 3,602,712 | 8/1971 | Mann et al. . |
| 3,617,178 | 11/1971 | Clouston . |
| 3,704,089 | 11/1972 | Stehlik . |
| 3,736,111 | 5/1973 | Gardner et al. . |
| 3,736,120 | 5/1973 | Tempe . |
| 3,742,180 | 6/1973 | Bradley . |
| 3,753,651 | 8/1973 | Boucher . |
| 3,783,217 | 1/1974 | Brown . |
| 3,795,183 * | 3/1974 | Roth et al. ............................. 99/353 |
| 3,861,117 | 1/1975 | DeFilippi . |
| 3,885,119 | 5/1975 | Sargeant . |
| 3,885,915 | 5/1975 | Utsumi et al. . |
| 3,926,379 | 12/1975 | Dryden et al. . |
| 3,926,556 | 12/1975 | Boucher . |
| 3,929,295 | 12/1975 | Montalbano . |
| 3,940,325 | 2/1976 | Hirao . |
| 3,948,601 | 4/1976 | Fraser et al. . |
| 3,958,765 | 5/1976 | Musselman . |
| 3,958,936 | 5/1976 | Knight, Jr. . |
| 4,072,273 | 2/1978 | Reiniger . |
| 4,140,537 | 2/1979 | Luck, I . |
| 4,148,614 | 4/1979 | Kirkbride . |
| 4,151,419 | 4/1979 | Morris et al. . |
| 4,175,885 | 11/1979 | Jeppson . |
| 4,205,794 | 6/1980 | Horton et al. . |
| 4,207,286 | 6/1980 | Gut Boucher . |
| 4,250,139 | 2/1981 | Luck, II . |
| 4,252,459 | 2/1981 | Jeppson . |
| 4,252,487 | 2/1981 | Jeppson . |
| 4,264,362 | 4/1981 | Houser . |
| 4,276,093 | 6/1981 | Pickermann . |
| 4,295,908 | 10/1981 | Schaefer et al. . |
| 4,341,353 | 7/1982 | Hamilton et al. . |
| 4,347,016 | 8/1982 | Sindelar et al. . |
| 4,374,491 | 2/1983 | Stortroen et al. . |
| 4,376,033 | 3/1983 | Calderon . |
| 4,376,034 | 3/1983 | Wall . |
| 4,398,076 | 8/1983 | Hanson . |
| 4,400,357 | 8/1983 | Hohmann . |
| 4,457,221 | 7/1984 | Geren . |
| 4,510,363 | 4/1985 | Reynolds, Jr. . |
| 4,524,079 | 6/1985 | Hofmann . |
| 4,546,226 | 10/1985 | Trembley et al. . |
| 4,552,720 | 11/1985 | Baker, Sr. et al. . |
| 4,563,259 | 1/1986 | Rayner . |
| 4,569,736 | 2/1986 | Kosegaki et al. . |
| 4,599,216 | 7/1986 | Rohrer, I . |
| 4,619,550 | 10/1986 | Jeppson . |
| 4,620,908 | 11/1986 | Van Duzer . |
| 4,652,763 | 3/1987 | Nablo . |
| 4,670,634 | 6/1987 | Bridges et al. . |
| 4,671,935 | 6/1987 | Rohrer, II . |
| 4,706,560 | 11/1987 | Capodicasa . |
| 4,710,318 | 12/1987 | Horiuchi et al. . |
| 4,732,680 | 3/1988 | Weaver et al. . |
| 4,746,946 | 5/1988 | Chan . |
| 4,746,968 | 5/1988 | Wear et al. . |
| 4,749,491 | 6/1988 | Lawes et al. . |
| 4,760,228 * | 7/1988 | Kudo ................................. 219/686 |
| 4,775,770 | 10/1988 | Fritz . |
| 4,801,427 | 1/1989 | Jacob . |
| 4,808,782 | 2/1989 | Nakagawa et al. . |
| 4,808,783 | 2/1989 | Stenstrom . |
| 4,818,488 | 4/1989 | Jacob . |
| 4,830,188 | 5/1989 | Hannigan et al. . |
| 4,874,134 | 10/1989 | Wiens . |
| 4,884,756 | 12/1989 | Pearson . |
| 4,896,010 | 1/1990 | O'Connor et al. . |
| 4,917,586 | 4/1990 | Jacob . |
| 4,931,261 | 6/1990 | Jacob . |
| 4,936,996 | 6/1990 | Messing . |
| 4,943,417 | 7/1990 | Jacob . |
| 4,974,781 | 12/1990 | Placzek . |
| 4,978,501 | 12/1990 | Diprose et al. . |
| 4,983,299 | 1/1991 | Lupton et al. . |
| 4,984,748 | 1/1991 | Kimura . |
| 4,988,044 | 1/1991 | Weitzmann et al. . |
| 5,019,344 | 5/1991 | Kutner et al. . |
| 5,035,858 | 7/1991 | Held et al. . |
| 5,048,766 | 9/1991 | Gaylor et al. . |
| 5,077,007 | 12/1991 | Pearson . |
| 5,106,594 | 4/1992 | Held et al. . |
| 5,184,780 | 2/1993 | Wiens . |
| 5,204,001 | 4/1993 | Tonelli et al. . |
| 5,226,065 | 7/1993 | Held et al. . |
| 5,232,596 | 8/1993 | Castaldi . |
| 5,254,253 | 10/1993 | Behmann . |
| 5,340,376 | 8/1994 | Cunningham . |
| 5,340,536 * | 8/1994 | Datar et al. ........................... 422/23 |
| 5,389,248 | 2/1995 | Pare et al. . |
| 5,408,074 * | 4/1995 | Warmbier et al. .................. 219/701 |
| 5,476,634 | 12/1995 | Bridges et al. . |
| 5,508,004 * | 4/1996 | Held et al. ............................ 422/22 |
| 5,523,052 | 6/1996 | Bridges et al. . |
| 5,523,548 | 6/1996 | Tsukagoshi et al. . |
| 5,589,140 * | 12/1996 | Takahashi ........................... 422/159 |
| 5,609,820 | 3/1997 | Bridges et al. . |
| 5,641,423 | 6/1997 | Bridges et al. . |
| 5,709,842 | 1/1998 | Held et al. . |
| 5,830,419 | 11/1998 | Held et al. . |
| 5,833,922 | 11/1998 | Held et al. . |

FOREIGN PATENT DOCUMENTS

| | | |
|---|---|---|
| 942374 | 11/1963 | (GB) . |
| 1406789 | 9/1975 | (GB) . |
| 2130060 | 5/1984 | (GB) . |
| 2166633 | 5/1986 | (GB) . |
| 63-227515 | 9/1988 | (JP) . |
| 01-034803 | 2/1989 | (JP) . |
| 01-144039 | 6/1989 | (JP) . |
| 1123705 | 11/1984 | (SU) . |

OTHER PUBLICATIONS

"Gamma Processing Equipment", AECL Industrial Irradation Division, (Jan. 1987).

Serota. "Heating With Radio Waves." *Automation* (Sep. 1973).

Center for Materials Fabrication. "Dielectric Heating: RF and Microwave." *TechCommentary,* vol. 4, No. 1 (1987), pp. 1–4.

Reynolds et al., "Thermoradiation Inactivation of Naturally Occuring Bacterial Spores in Soil." *Applied Microbiology,* vol. 28, No. 3 (Sep. 1974), pp. 406–410.

Brannen. "A Kinetic Model for the Biological Effects of Ionizing Radiation." Report No. SAND74–0269, Sandia Laboratories, Albuquerque, New Mexico, printed Oct. 1974, pp. 1–38.

1976 Progress Report—"Beneficial Uses Program–Period Ending Dec. 31, 1976." Report No. Sand 77–0426, Sandia Laboratories, Albuquerque, New Mexico, printed Mar. 1977, pp. 3–44.

"Dielectric Heating", PSC, Inc., published prior to Jan. 27, 1999.

Sivinski. "General Description of the Sludge Irradiation Process." National Symposium on the Use of Cesium–137 to Process Sludge for Further Reduction of Pathogens (held in Denver Colorado, Sep. 3–4, 1980). Published Dec. 1980, pp. 57–68.

Tonetti. "Disease Control Requirements for Various Sludge Uses." National Symposium on the Use of Cesium–137 to Process Sludge for Further Reduction of Pathogens (held in Denver, Colorado, Sep. 3–4, 1980). Published Dec. 1980, pp. 43–56.

"Electromagnetic Radiation and Ionizing Energy." (unknown source. Published prior to Jan. 27, 1999), pp. 6–8, 32–33, and 35–50.

Ward. "Molecular Mechanisms of Radiation–Induced Damage to Nucleic Acids." (unknown source. Published prior to Jan. 27, 1999), pp. 181–239.

Markitanova et al., "Study of Reagentless Sterilization of Wastewaters." *Journal of Applied Chemistry of the USSR,* vol. 59, No. 11/part 2 (Nov. 1986), pp. 2365–2368.

Hall, S.K. "Infectious Waste Managements: A Multi–Faceted Problem." *Pollution Engineering* (Aug. 1989), pp. 74–78.

*United States Pharmacopoeia* XX: Section 1211, "Sterilization," pp. 1037–1040.

Morganstern. "The Future of Radiation Sterilization." Second Johnson & Johnson Conference on Sterilization of Medical Products by Ionizing Radiation (held in Vienna, Austria, Apr. 25–28, 1977), pp. 1–26. Published Jun. 15, 1977.

*Sterling's Elutriator.* Sterling Systems, A Division of The Sterling Blower Company, Forest, Virginia. Published Jun. 1989.

*Innovative Technology From the Sterling Blower Company;* Sterling Systems, A Division of The Serling Blower Company, Forest, Virginia. Published Jun. 1989.

Boucher, "Advances in Sterilization Techniques–State of the Art and Recent Breakthroughs", Amer. Jour. of Hospital Pharmacy, vol. 29, Aug. 1972, pp. 661–672.

"Induction and Dielectric Heating," by Cable, J. Wesley, published by Reinhold Publishing Corp., New York, New York (1954), pp. 501–512.

Report Entitled: Biosolution's Pulluton Compliance System Demonstration at United Parcel Service, Sheronville, Ohio Facility, believed to be publically available prior to Jan. 27, 1999.

Copy of International Search Report for PCT/US99/11536 dated Aug. 18. 1999.

* cited by examiner

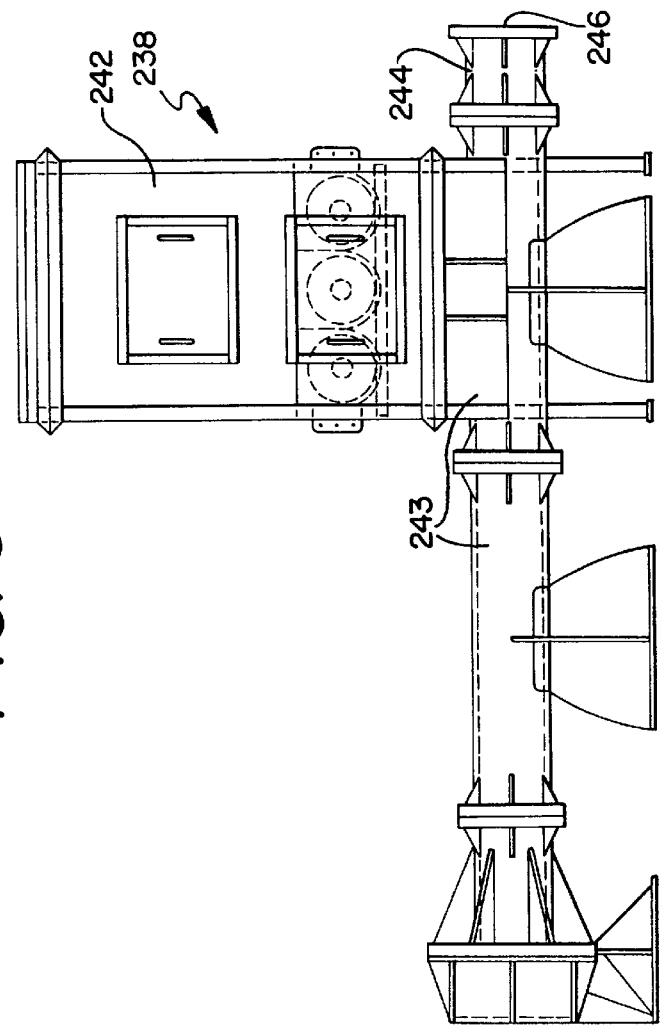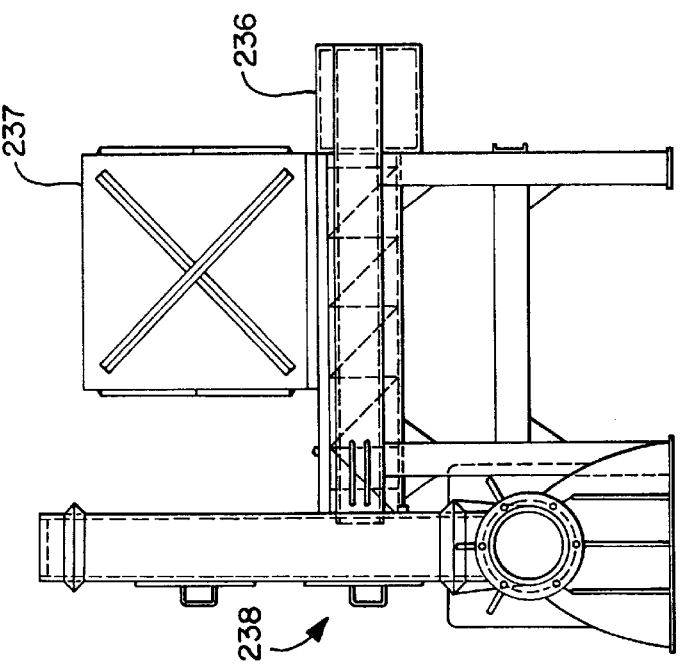

APPARATUS AND METHOD FOR THE DISINFECTION OF MEDICAL WASTE IN A CONTINUOUS MANNER

BACKGROUND OF THE INVENTION

Medical waste disposal is of urgent concern because the waste may cause infection. Such infectious waste is a by-product of medical and veterinary care. For example, regulated medical waste consists of the following categories:

1. Cultures and stocks of infectious agents and associated biologicals;
2. Pathological wastes;
3. Human blood and blood products;
4. Contaminated "sharps", including needles, syringes, blades, scalpels, and broken glass;
5. Animal waste;
6. Isolation waste, including gloves and other disposable products used in the care of patients with serious infections; and
7. Unused "sharps".

Hospitals typically segregate these categories of waste into three general groups: a) general medical waste, including waste listed above in categories 1, 2, and 3; b) veterinary waste, or category 5; and c) waste that is predominantly plastic, including categories 4 and 6. Contaminated sharps and isolation waste are categories of special concern, as this waste may have been exposed to highly dangerous infections such as AIDS or hepatitis. Sharps in particular have caused deep public concern when observed on beaches and other public areas.

Hospitals and other generators of medical and veterinary waste employ three main methods of waste handling: 1) on-site incineration of the waste, 2) on-site steam autoclaving of the waste and later shipment to a landfill, and 3) no on-site processing before turning the waste over to a waste hauler.

Predominantly located in urban areas, many hospital incinerators emit pollutants at a relatively high rate. In the emissions of hospital incinerators, the Environmental Protection Agency (EPA) has identified harmful substances, including metals such as arsenic, cadmium, and lead; dioxins and furans; organic compounds like ethylene, acid gases, and carbon monoxide; and soot, viruses, and pathogens. Emissions from these incinerators may be a bigger public health threat than improper dumping. (Stephen K. Hall, "Infectious Waste Management: A multi-faceted Problem," Pollution Engineering, 74–78 (August 1989)).

Although steam autoclaving may be used to disinfect waste before further processing, it is expensive and time-consuming. Heat rapidly inactivates viruses; but bacteria survive somewhat longer than viruses. Bacterial spores can be highly resistant to heat sterilization. To assure effective disinfection, temperature monitoring devices such as thermocouples and biological indicators such as heat-resistant *Bacillus stearothermophilus* spores may be used.

U.S. Pat. No. 2,731,208 to Dodd teaches a steam-sterilizing apparatus for disposing of contaminated waste which shreds waste ("including paper containers such as used sputum cups," Col. 1, lines 28–29), blows steam into a container full of shredded waste and pours the disinfected waste into a sewage system. This process has several drawbacks, including processing of only limited types of items and depositing the processed waste into a sewer (Col. 4, line 49).

Soviet Union Inventor's Certificate No. 1,123,703 also discloses a method of sterilizing medical instruments for reuse by UHF treatment. For injection needles it discloses a final temperature of 160° to 470° C. and for acupuncture needles it discloses a final temperature of 160° to 270° C.

U.S. Pat. No. 3,958,936 to Knight teaches compaction of hospital waste for more efficient landfill disposal. Specifically, this reference teaches the application of heat in the range of about 400° to 600° F. to hospital and other waste to melt the plastic and turn it into a hard, compact block for safer disposal in landfills. The waste is disinfected and needles become imbedded in the plastic. This method has the disadvantages of requiring high energy expenditure to attain high temperatures and landfill disposal.

U.S. Pat. No. 3,547,577 to Lovercheck discloses a portable device for treating garbage such as trash, domestic refuse and the like (Col. 1, lines 13–19). The machine shreds garbage, compresses the shredded garbage into briquettes, and sterilizes the briquettes with ethylene oxide gas (Col. 1, lines 15–19). After shredding, the garbage may be separated into magnetic and non-magnetic portions (Col. 2, lines 13–23). After the garbage is so separated, only the non-magnetic portion is compressed into briquettes and sterilized (Col. 2, lines 23–25). The sterilization step employs ethylene oxide gas which requires temperature control (Col. 2, lines 30–57). Thus, the briquettes are maintained at a temperature of about 54° C. (Col. 2, line 51). A drawback of this system is that both heat and poisonous gas are required to disinfect the garbage. Another drawback is that when the waste stream is divided into metal, water and briquettes, only part of the waste stream (the briquettes without metal or water) is disinfected. An additional disadvantage is that the volume of the waste stream is limited in that only one briquette is formed at a time. Another drawback is that the material is disposed in a landfill or by incineration. Although use as a fertilizer is suggested (Col. 1, line 47), there is no teaching that the briquettes are really suited for that use or how the briquettes could be further processed for that use.

Various energy sources are being considered as potential sterilants. Microwaves are increasingly being investigated for rapid sterilization of individual medical devices and shredded medical waste. Recently, an experiment showed that metallic instruments could be disinfected in only 30 seconds in a microwave chamber. (*N.Y. Times*, "Science Watch: Microwave Sterilizer is Developed," Jun. 20, 1989). A problem is that this particular method can handle only a few instruments at a time.

According to one publication, a medical waste disposal system utilizing microwaves has apparently been developed. This system first shreds medical waste, sprays it with water and spreads the small pieces in a thin layer on a conveyor belt. Then, the conveyor carries the mixture through a microwave chamber which heats the mixture to about 96° C. The waste can be routed to a steaming station where steam is applied to inactive surviving microorganisms. After the disinfection step, the waste is packaged for shipment to landfills or incinerators. (*The Wall Street Journal*, p. B3, Apr. 10, 1989).

Further, microwaves are limited in their penetration. If applied to large-scale, boxed medical waste, the microwaves alone do not heat very effectively. In contrast, radio-frequency (RF) waves are relatively low-frequency waves which penetrate more effectively. RF waves have been used directly and indirectly for sterilization.

U.S. Pat. No. 3,948,601 to Fraser et al. teaches the indirect use of RF waves in disinfecting a wide variety of medical and hospital equipment as well as human waste. This reference teaches the use of RF waves to heat certain gases (particularly argon) to ionize into gas plasma at approximately 100° to 500° C. This references teaches that "cool" plasma (Col. 1, line 12) effectively sterilizes an article at a temperature of only 25° to 50° C. and very low pressure. However, sterilization by plasma gas does not suggest the direct use of RF waves in sterilization.

Whether or not the hospital first autoclaves its medical waste, including broken needles and glass, the waste is then turned over to a waste handler for transport to a landfill or other depository. There are several problems with this disposal method. First, landfills, particularly in many urban areas, are becoming filled. In addition, older landfills may leak toxic chemicals into the surrounding earth and contaminate the water supply. Thus, burying wastes is becoming more of a concern. Also, unauthorized dumping may occur.

SUMMARY OF THE INVENTION

One aspect of the present invention relates to a method of processing medical waste which includes the steps of continuously feeding medical waste into a tube and exposing the medical waste passing through the tube to electromagnetic radiation so as to heat and disinfect the medical waste.

A second aspect of the present invention relates to an apparatus for processing medical waste with an extruder that receives medical waste and forms a continuous tube of the medical waste for feeding through a source of electromagnetic radiation. The source of electromagnetic radiation receives the continuous tube of the medical waste and generates electromagnetic radiation that heats and disinfects the continuous tube to produce a disinfected continuous tube of the medical waste.

A third aspect of the present invention relates to a method of reducing the potential of ignition of a fire of a material to be disinfected by radio-frequency radiation by providing a material to be disinfected and continuously feeding the material into a tube, wherein a portion of the tube is positioned in a field of radio-frequency radiation. The material passing through the tube is exposed to the radio-frequency radiation so as to heat and disinfect the material.

Each aspect of the present invention provides an efficient apparatus and method to reduce the infectious potential of medical waste and to transform it into material which would not adversely impact the overall environment. The present invention provides improved throughput of medical waste per unit volume in addition to improved reduction of arcing, ignition of fires and radio-frequency field enhancements. Each aspect of the present invention also provides improved thermal performance by creating steam thereby pre-heating the material which aids in sustaining the material's temperature. In addition, a preferred embodiment of the present invention allows for further transformation of pre-sorted medical and veterinary waste into either recycled plastic or refuse-derived fuel.

Additional advantages and novel features of the invention will be set forth in part in the description which follows, and in part will become apparent to those skilled i he art upon examination of the following or may be learned by practice of the invention.

BRIEF DESCRIPTION OF THE DRAWINGS

FIG. 7 is a front view of an embodiment of an extruder to be used with the apparatus of FIG. 2; and FIG. 8 is a side view of the extruder of FIG. 7.

DETAILED DESCRIPTION OF THE PRESENTLY PREFERRED EMBODIMENTS

Disintegrating or Shredding the Waste

Figure 1:
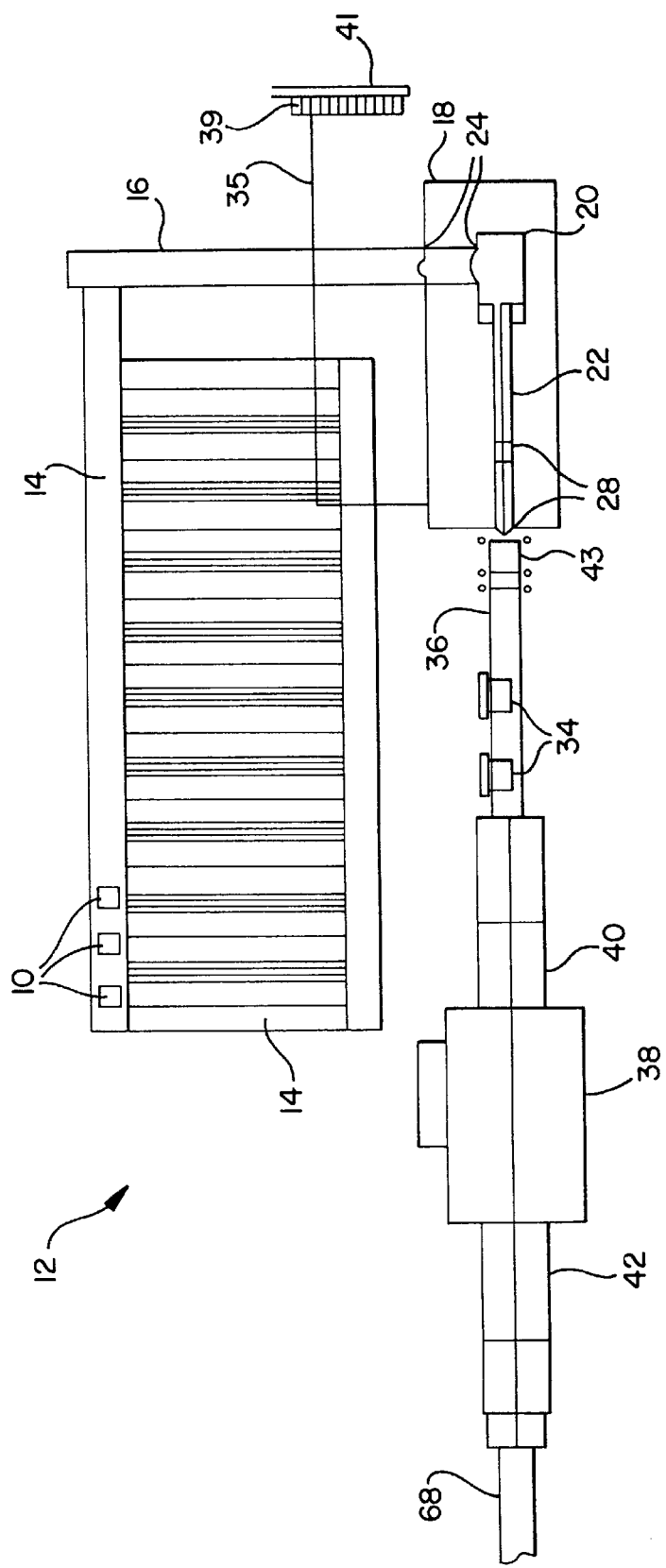
FIG. 1 shows a plan view diagram of a first embodiment of an apparatus for handling and processing of medical and veterinary waste.

As shown in FIG. 1, medical waste in sealed boxes 10 arrives at the medical waste processing facility 12 and is unloaded onto a conveyor belt 14 where all boxes 10 in each load are segregated and counted. The shredder load conveyor 16 carries the boxes 10 into the pre-processing room 18. The pre-processing room 18 contains a shredder 20 and a screw conveyor 22 which are designed to disintegrate medical waste into fragments and move the fragments to other containers 34 for disinfection. As herein defined, disintegration refers to breaking up or shredding materials to a relatively uniform size that is no larger than about 1½ inches.

Figure 3:
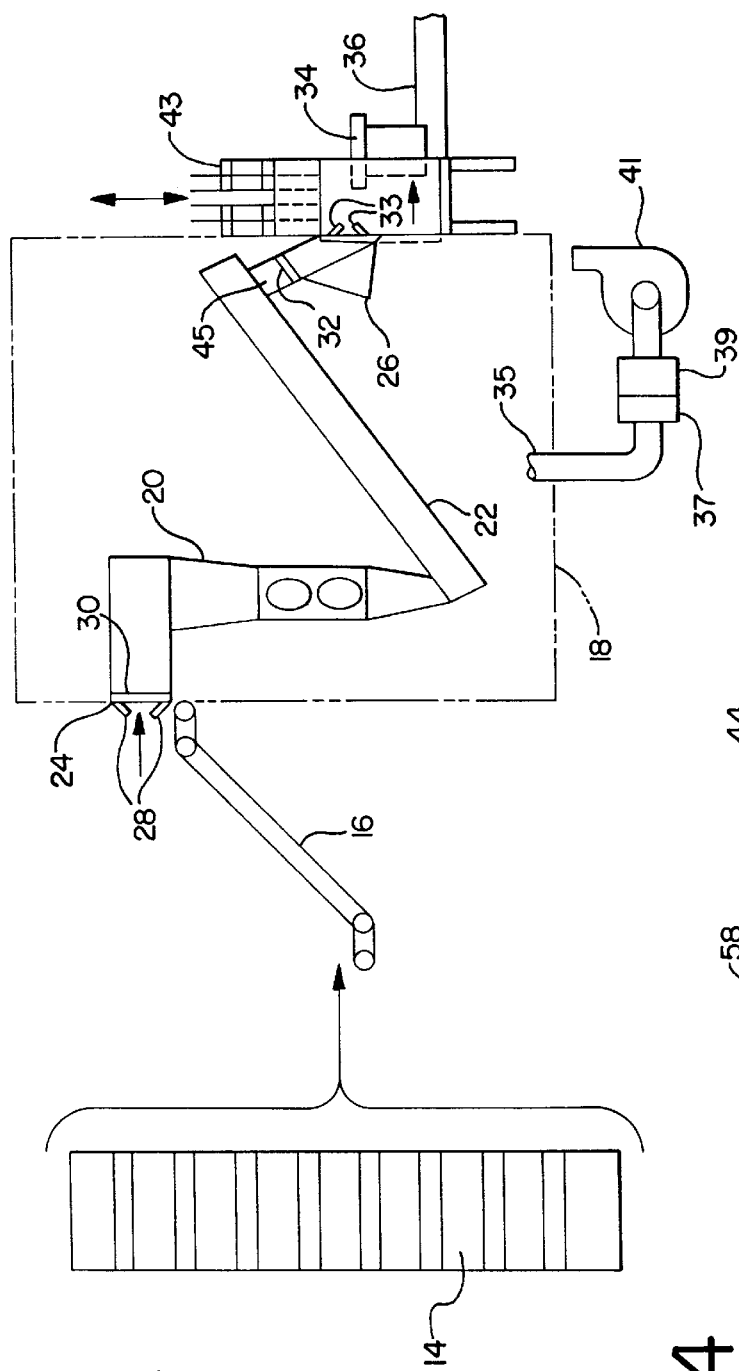
FIG. 3 schematically shows an embodiment of a pre-processing apparatus to be used with the apparatuses of FIGS. 1 and 2.

As schematically shown in FIG. 3, the pre-processing room 18 has several features to prevent the escape of contamination from the room 18. First, entry and exit of medical waste in the pre-processing room 18 is controlled by two sets of airlocks, inlet airlocks 24 and outlet airlocks 26. Each set of airlocks consists of two sets of doors, 28, 30 and 32, 33, respectively. To enter the pre-processing room 18, the boxes 10 of medical waste pass through the first set of doors 28, which closes behind the boxes 10. After the first set of doors 28 closes, the second set of doors 30 opens and permits the boxes 10 to enter the pre-processing room 18. The exit doors 32, 33 operate similarly to the inlet doors 28, 30. Thus, there is always at least one set of exit and entry doors closed at any time.

In addition to the airlocks 24 and 26, airflow is further controlled by heated and filtered room exhaust ducts 35. Electric duct heaters 37 keep the temperature in the ducts 35 at about 82° C. which significantly reduces the population of viruses. Across the ducts 35 are high-efficiency particulate air (HEPA) filters 39 having pores of 3 microns and an efficiency of 99.7% in preventing bacteria from escaping. These room exhaust ducts 35 control the airflow into and out of the sealed pre-processing room 18. One large fan 41 pulls air out of these ducts 35 at the rate of about 1,000 cubic feet per minute. This fan produces "negative" air pressure which helps prevent possibly contaminated air from the pre-processing room 18 from flowing back into the rest of the facility 12. The heated, filtered air is vented to the outside environment.

In addition to the room exhaust duct 35, there are heated, filtered ducts (not shown) connected to the shredder 20, the screw conveyor 22 and the pneumatic press 43 which vent to the outside environment in the same fashion as described for the room exhaust ducts 35.

As shown in FIG. 3, the boxes 10 of medical waste enter the pre-processing room 18 on conveyor 16 and are emptied into shredder 20. The disintegration or shredding is performed by two sets of cutting blades (not shown) rotating at 1800 revolutions per minute which are powered by 50-horsepower motors (not shown). The shredder 20 turns the medical waste into fragments which measure about 1.5 inches in their greatest dimension. Shredding also reduces the volume of the medical waste by about one half. A suitable shredder is Model No. 00-5371-D available from Shredding Systems, Inc., Wilsonville, Oreg., which measures about 12 feet tall, 10 feet wide and 12 feet long.

According to one embodiment, the waste fragments exit the shredder 20 via a screw conveyor 22 which operates inside a tube and which further carries the medical waste fragments vertically to the conveyor tube 45 from which the fragments drop into the pneumatic press 43. The pneumatic press 43 compresses the medical waste fragments into heat-resistant plastic polyethylene containers 34 which measure 24 inches by 24 inches by 18 inches and weight about 50 pounds. As defined herein, heat-resistant means that the containers do not soften or melt during the heating process and that the containers keep the temperature of medical waste within about 8° C. when stored at room temperature (25° C.) for one hour. The containers 34 include snug but not air-tight lids. A suitable container is Model No. 24, available from Chem-Tainer, Babylon, N.Y. Each container 34 is filled with about 200 pounds of compacted waste fragments. At this point in the process, water may be added, but is not usually necessary. Alternately, a foam may be sprayed on medical waste fragments having a high metallic content. Water and foam are thought to help disperse the heat and avoid fires. Then, a cover is attached snugly to the filled container 34.

The pneumatic press 43 further compacts the medical waste fragments to less than one half the volume the container 34 receives. Hence, the total reduction in medical waste volume from receipt at the facility 12 to closing of the container 34 is about five to one. In this manner, wastes which enter the pre-processing room 18 with a density of five (5) pounds per cubic foot exit the room 18 at densities of 25 pounds per cubic foot. It can be seen that dissimilar wastes, namely paper, plastics, glass, metal and fluids are converted into the more uniform sizes and densities required for a mechanized radio-frequency (RF) heating chamber.

Figure 2:
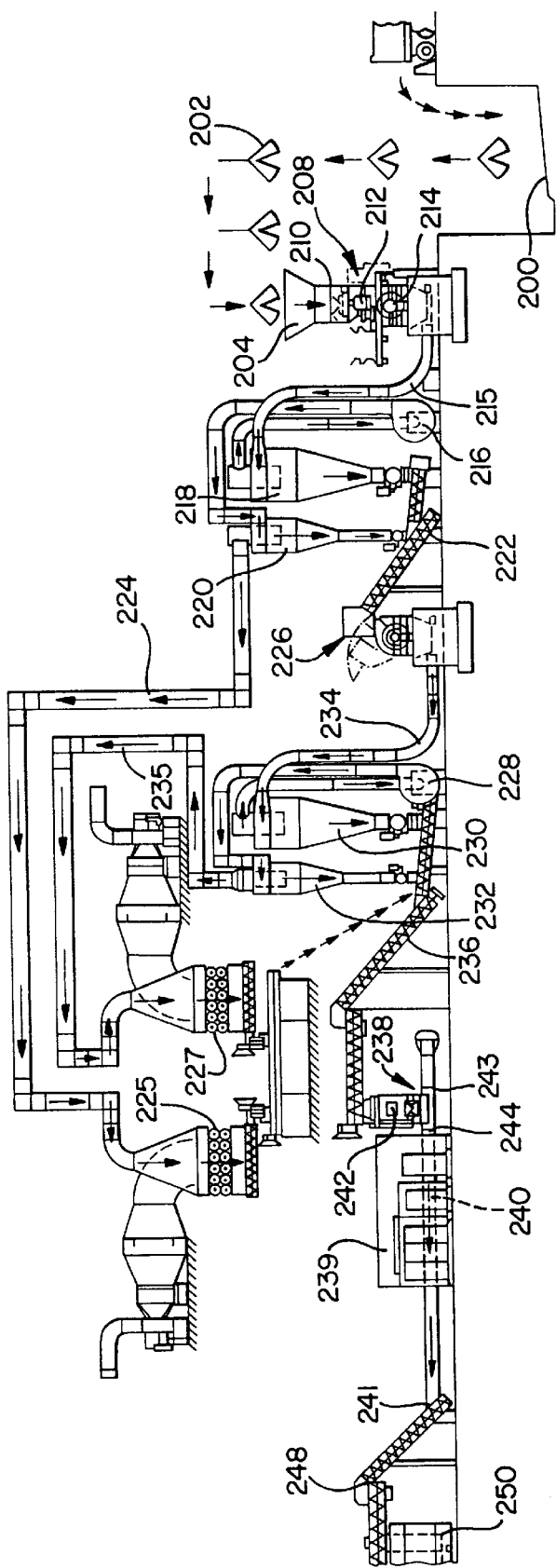
FIG. 2 shows a plan view diagram of a second embodiment of an apparatus for handling and processing of medical and veterinary waste according to the present invention.
Figure 2A:
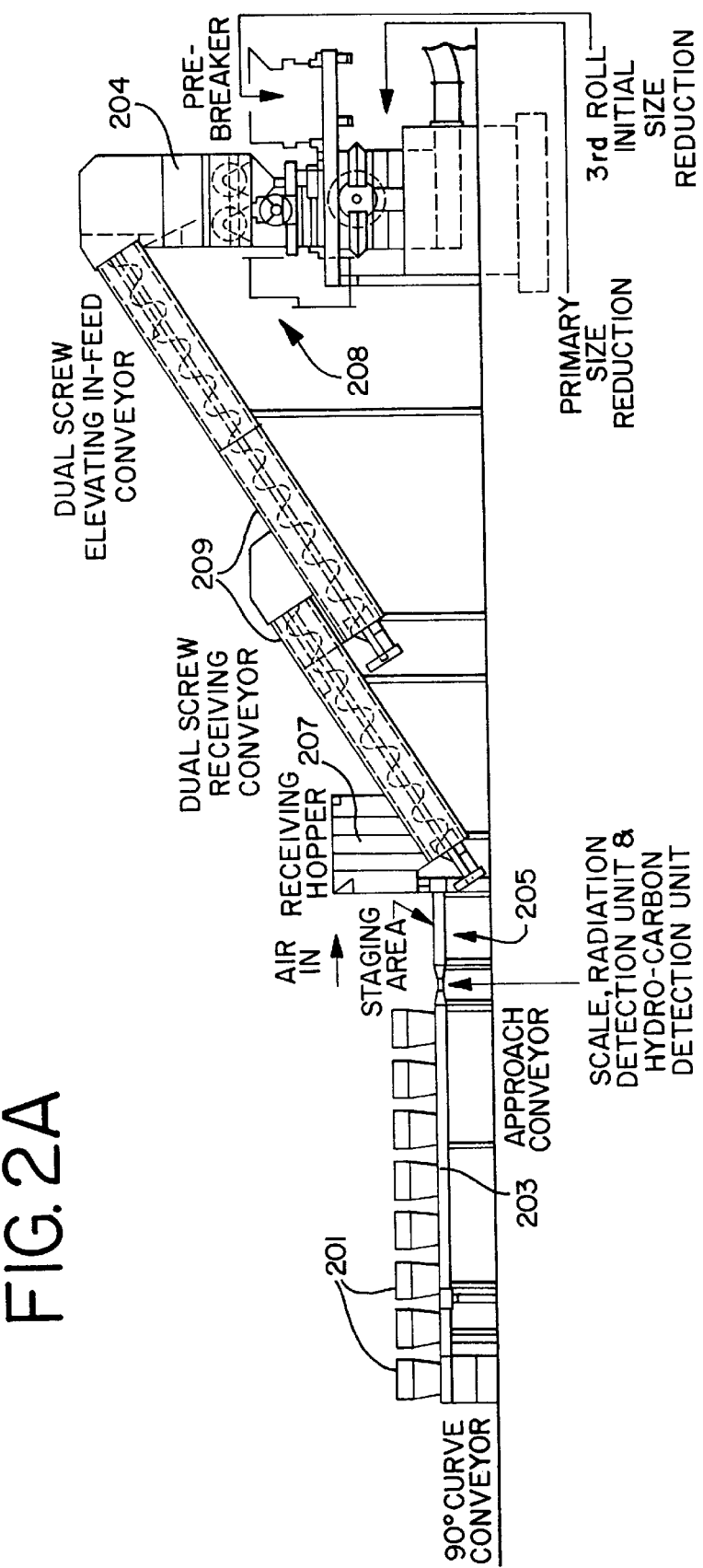
FIG. 2A shows a plan view of an alternative waste input system for use in the apparatus of FIG. 2.

In a second preferred embodiment, the waste is processed essentially as described above except that the waste is not processed in separate containers. In this embodiment, as best shown in FIG. 2, medical waste is received in a collection pit 200. A material transfer device 202 is used to remove the medical waste from the collection pit 200 and place it in a receiving hopper 204. The hopper 204 discharges the waste into a waste size reduction unit 208. Within the waste size reduction unit 208, a pair of counter-rotating feed control rolls 210 volumetrically meters the transfer of material to the initial size reduction assembly 212. The material is then torn into strips and pieces in the initial size reduction assembly 212 and then passes through a primary size reduction assembly 214 which may be any standard, commercially available size reduction device (e.g., shredder). The material is ground to a uniform size in the primary reduction assembly 214. The uniform size is a predetermined size that may be preset to comply with local regulations. Preferably, the waste size reduction unit 208 has a multi-stage, variable clearance, high speed attrition design. Suitable waste size reduction units include open or closed rotor granulators, hammer mill-type ore crushers, wood hogs, automobile crushers or tree chippers adapted so that the interior attrition surfaces are configured, as is known to those of ordinary skill in the art, to account for characteristics such as size and abrasion resistance of the material to be processed. In another embodiment, as shown in FIG. 2A, medical waste may be received in containers 201 on an approach conveyor 203. The waste containers 201 pass over a staging area 205 having a scale, radiation detector, and hydrocarbon detector and proceed into a receiving hopper 207. The waste is dumped from the containers 201 and transported by dual-screw conveyors 209 to the hopper 204 on the waste size reduction unit 208.

A primary fan 216 maintains the hopper 204 and size reduction process under negative pressure to keep aerosols from escaping the waste processing equipment. The primary fan is preferably at least a 7,500 cubic feet per minute (CFM) high pressure fan which produces a total static pressure of 16–20 inches (water column). Other fans and pressures may also be used. Following the size reducing process of the waste size reduction unit 208, the material is transferred in a high velocity airflow along a tube 215 to a primary low energy cyclone 218 that uses centrifugal force to separate the material from the high velocity airflow. The high velocity transport air passes through the primary fan 216 into a primary high energy cyclone 220 that removes fugitive dust particles and deposits them onto the sealed material conveyor 222. The transport air then passes along a dust transfer duct 224 and exits the process room through a dust control unit 225 after three more stages of filtering and an odor control step. The dust control unit may be any standard, commercially available bag or cartridge filter unit.

The material transport conveyor 222 takes the shredded waste processed by the primary low and high energy cyclones 218, 220 to a secondary waste size reduction unit 226 for grinding the material into small uniform pieces. A secondary fan 228 generates a high velocity airflow that pulls the shredded material through a transfer tube 234. A secondary low energy cyclone 230 and a secondary high energy cyclone 232 removes fugitive dust particles from the high velocity air flow. The high velocity air flow generated by the secondary fan passes through a dust transfer duct 235. The dust transfer duct 235 leads to a secondary dust control unit 237. The secondary size reduction unit 226, and the dust control 237 may be of the same construction as the primary size reduction unit 208 and dust control unit 225, respectively.

The high energy cyclones 220, 232 each connect to a respective dust transfer duct 224, 235 that feeds into a respective dust control unit 225, 237. The dust control units 225, 237 preferably include three filter stages (not shown), a continuous cleaning dust filter, a HEPA pre-filter, and a HEPA filter bank. These filters remove particulates from the air that exits the waste processing facility. The effectiveness of the various air control devices is preferably:

| Device | % Effectiveness | |
| --- | --- | --- |
| Primary low energy cyclone | 90% | >20 microns |
| Primary high energy cyclone | 95% | >10 microns |
| Secondary low energy cylcone | 90% | >20 microns |
| Secondary high energy cyclone | 95% | >10 microns |
| HEPA pre-filter | 95% | >5 microns |

| Device | % Effectiveness | |
| --- | --- | --- |
| Continuous cleaning dust filter | 99.999% | >1 micron |
| HEPA filters | 99.9999% | >0.12 micron | where the percent effectiveness defines the percentage of particles greater than a given size that are removed from the air.

The finely ground waste material, any dust collected, and any process waste water which may be produced are deposited on a material transport conveyor 236 that conveys the material to a high density extruder 238. The extruder 238 compresses the moistened medical waste fragments and concurrently pushes the compressed waste into a fixed tube 240 for disinfection. The tube 240 is preferably constructed of a rigid composite material. One suitable composite material is filament wound E-Glass embedded in a fire resistant resin. The extruder 238 performs a multi-stage, and preferably two stage, mechanical compression of the waste, such as through piston and cylinder assemblies. The extruder 238 is preferably constructed of abrasion resistant steel.

Referring to FIGS. 7 and 8, a hopper 237 receives the waste materials from the conveyor 236 and deposits them into the extruder 238. The extruder 238 has two compression chambers for compressing the waste material in two stages. The primary compression stage 242 is located in a vertically oriented chamber. The primary compression stage 242 increases the density of the waste approximately 2:1. One suitable piston cylinder for the primary compression stage 242 is an N5 series hydraulic cylinder, model no. N5R3.25×23-C-1.75-2-S-H-R-1-1, available from Hydro-Line. The final compression stage 243, horizontally positioned in the end of an extruder throat 244, compresses the waste a second time and continuously presses the waste through the extruder throat 244. The final compression stage increases the density of the material compressed from the primary stage by approximately 2–3:1 such that the total compression after the final stage is 4–6:1. An N5S-5×62-C-3.5-2-F-J-R-1-1-X N5 series hydraulic cylinder from Hydro-Line may be used for the second compression stage 243. The fully compressed waste is continuously pressed t rough the extruder throat 244 and out an exit end 246. The extruder throat 244 feeds directly into the fixed tube 240 that is positioned in the dielectric heater (FIG. 2). Advantages of using the extruder 238 and the fixed tube 240 include improved energy usage through improved dielectric coupling, reduction of the possibility of fire due to reduced air content of the waste, and improved dielectric performance through generating a more uniform dielectric constant in the waste material. Also, because the occurrence of air pockets is reduced in the medical waste, the dielectric constant of the medical waste is increased.

Disinfection

In the first embodiment, as shown in FIG. 1, the sealed containers 34 of medical waste fragments are transported away from the pre-processing room 18 and into the dielectric heater 38 for volumetric heating by electromagnetic radiation, such as radio-frequency (RF) radiation. The containers 34 of compacted medical waste fragments enter the dielectric heater 38, and do so through an entry tunnel 40. The dielectric heater 38 generates RF waves, which heat the waste as described below. The waste fragment containers are uniformly or volumetrically heated in the electric field for about five minutes. As a result of this exposure to RF waves, the waste reaches temperatures of about 90°–100° C.

The covered containers 34 move along a conveyor 36 into the dielectric heater 38 which measures 38 feet long, 13 feet wide and 10 feet high. The dielectric heater weighs 28,000 pounds. Two eight-foot tunnels 40 and 42, form the entry and exit portions respectively, of the dielectric heater 38. The tunnels attenuate RF waves and prevent RF leakage from the dielectric heater 38. In the 20-foot-long RF chamber or oven 44, a system of exciter and ground electrodes 46 generate electromagnetic waves in the RF band. The RF band is between audio and infrared frequencies and includes approximately 10 kilohertz (kHz) to 300 gigahertz (GHz). When the electrode system 46 is supplied with radio frequency power, it projects an electromagnetic wave into the target containers 34 of medical waste.

In the second preferred embodiment, as shown in FIG. 2, the compressed medical waste fragments are disinfected as the extruder 238 steadily pushes them through the fixed tube 240. After disintegrating the medical waste and compressing the waste in the extruder 238, the extruder pushes the compressed medical waste fragments into the first end of the tube 240. The tube 240 extends from the extruder 238 through the dielectric heater 239 and out the exit end of the dielectric heater. In one embodiment, the entering end of the tube 240 may be 12 inches in diameter. This diameter increases a constant amount per distance length of tube 240. In one embodiment, the diameter increases a constant amount somewhere between one-eighth to one-half inch per foot length of tube. The waste is continuously pushed through the tube 240 and moves along the tube through the dielectric heater 38 for volumetric heating by RF waves.

The compacted medical waste fragments enter the dielectric heater 239 through the tube 240. The dielectric heater 239 generates RF waves, which heat the waste as described above. The waste fragments are moved at a constant rate through the tube 240, and thus through the heater. The waste is uniformly or volumetrically heated in the electric field for about three to ten minutes depending on the strength of the electric field. The amount of time the waste remains in the electric field is designed so that the waste reaches temperatures of about 90°–100° C. as a result of the exposure to RF waves. Accordingly, the constant speed that the waste is pushed through the tube 240 may be adjusted based on the size and strength of the field generated in the dielectric heater. Preferably the dielectric heater exposes the tube of compressed medical waste fragments to an electric field oscillating at 11 megahertz (MHz) and having a field strength of 50 kilovolts per meter (kV/m).

The fixed tube is transparent to the electromagnetic radiation of the dielectric heater such that the RF waves effectively penetrate the composite material of the fixed tube 240 and substantially all of the energy is absorbed by the tube of waste. An advantage of using a fixed tube of composite material positioned in the dielectric heater rather than using multiple containers constructed of a polyethylene material is that that the tube may have a longer operational life than the containers 34. Additionally, the tube permits true continuous processing of the medical waste rather than a constant batch process.

Without being constrained to any particular theory, it is believed that, for the embodiments of FIGS. 1 and 2, the RF radiation transfers energy directly into materials, primarily by the interaction of their time-varying electric fields with molecules so as to produce heat inducing dipole rotation and molecular vibration. RF radiation or waves may be generated by connecting a RF alternating current to a pair of electrodes. Between the two electrodes, an alternating RF electromagnetic field having a time-varying electric field component is established. When objects are placed between the electrodes in the time-varying electric field, the time-varying electric field partially or completely penetrates the object and heats it.

Heat is produced when the time-varying electric field accelerates ions and electrons which collide with molecules. Heat also is produced because the time-varying electric field causes molecules, and particularly those with a relatively high electric dipole moment, to rotate back and forth as a result of the torque placed upon them by the time-varying electric field. Most large molecules, or molecules with evenly distributed charges, have relatively low or nonexistent dipole moments and are not very much affected by the RF time-varying electric field. Small molecules, in particular polar groups, have relatively large electric dipole moments and thus have relatively large torques exerted upon them by the time-varying electric field. In particular, highly polar molecules, like water, experience relatively large torques and as a result are rotated by the time-varying electric field. The mechanical energy of rotation is transferred to surrounding materials as internal energy or heat. Lower frequency time-varying electric fields penetrate deeply and heat objects more evenly. Relatively high frequency time-varying electric fields do not penetrate as deeply, but heat more rapidly the portions of objects they interact.

Because different materials are composed of different types of molecules with differing electric dipoles, they heat at different rates when exposed to a given RF field. For example, plastics, which are composed of very large molecules (polymers), are not heated by RF fields as rapidly as water. Metal objects may or may not be easily heated when exposed to RF fields, because their high conductivity tends to short out the electric fields and rescatter them. As a consequence, there are many conditions under which metal objects are difficult to heat. On the other hand, such RF fields can also induce substantial currents which flow on the outside of the metal objects. Under certain circumstances, heating effects will occur on the surface of the metal object which, in the case of a small needle, the heat is readily diffused into the interior. In addition, the presence of long, thin metal objects in an electric field causes enhancement of the electric field intensity near the ends of these metal objects and a diminution or shadowing of the fields near the middle. Thus, if the electric field is parallel to the axis of the metal object, strong electric fields will exist near the tips and weak electric fields will exist near the center of the rod or needle. Such field enhancements can lead to arcing and possible fires.

When RF waves are absorbed in both embodiments of FIGS. 1 and 2, they may cause differential heating. Moist articles and metal objects in the containers 34 or the tube 240 absorb more waves and may create "hot spots," or uneven heating; but prior disintegration and compaction of the medical waste fragments avoids serious arcing and speeds heat transfer. In the container 34 or the tube 240, steam and heat from the hotter fragments are rapidly redistributed to all the contained medical waste. Since the containers 34 are not airtight, and the tube 240 is open on both ends, steam gradually escapes and there is no excessive pressure buildup.

In the second embodiment of FIG. 2, the medical waste continues along the tube 240 after passing through the dielectric heater 239. After exiting the dielectric heater 239, the tube of disinfected medical waste emerges from the fixed tube 240 onto a conveyor 248 that deposits the disinfected waste into a container 250. Subsequently, the disinfected waste continues on to the other stations for additional processing as described in detail below. Alternatively, the tube of waste that emerges from the exit end of the fixed tube 240 may be held in a room or other containing space area (not shown) to cool to ambient temperature before further processing as described below.

Figure 4:
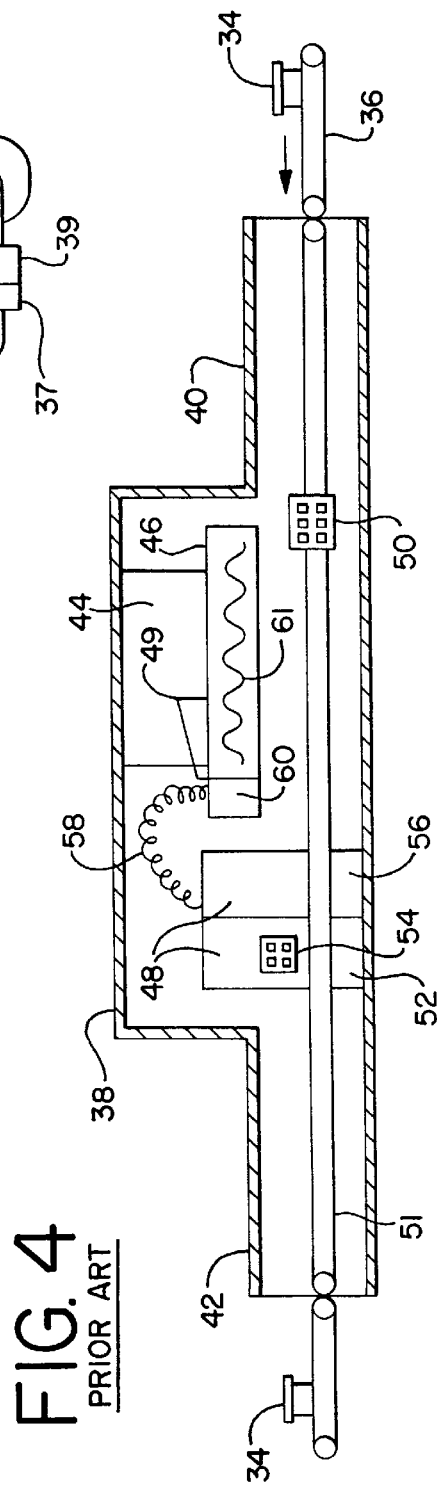
FIG. 4 schematically shows an embodiment of a radio-frequency heater to be used with the apparatuses of FIGS. 1 and 2.

As shown in FIG. 4, the dielectric heater 38, 239 for the embodiments of FIGS. 1 and 2 has the following components: a generator 48, an applicator 49 and controls 50. The generator 48 has a power supply 52, voltage controls 54 and a radiator source 56. The generator 48 measures 14.5 feet long, 3.5 feet wide and 7 feet high. It is fabricated of 10-gauge steel and aluminum with a four-inch channel base and a 0.25-inch thick steel base plate. The generator 48 has two dust-tight compartments with doors. These compartments contain the power supply 52 and radiator source 56. The power supply 52 and voltage controls 54 provide high-voltage direct current to the radiator source 56. Preferably, the generator 48 generates about 50 to about 150 kilowatts of power. More preferably, about 100 to about 150 kilowatts of power are generated. The power supply 52 compartment includes a 300 kilowatt, three-phase power transformer (not shown), which converts 60-cycle alternating current to direct current, as well as six stack silicon diode rectifiers and other equipment (not shown).

The radiator source 56 generates high-frequency power. Preferably, the frequency is in the range of about 5 to about 100 MHz. More preferably, the frequency is in the range of about 5 to about 25 MHz. Most preferably, the frequency is about 13 MHz when using the individual containers 34 (FIG. 1) and about 11 MHz when the fixed tube 240 (FIG. 2) is used. An oscillator (not shown) is preferred to generate the high-frequency power, although an amplifier (not shown) also may be used. A suitable oscillator is Model No. 3CW150000 from Eimac (Division of Varian, 301 Industrial Way, San Carlos, Calif.). An alternate for this purpose is Siemens Model No. RS3300CJ oscillator which is available from Siemens Components, 186 Wood Avenue, Islin, N.J. The radiator source also has a water supply (not shown) of approximately 25 gal/min at about 20° C. for cooling. A coaxial cable 58 feeds high-frequency power from the radiator source 56 into the heater applicator 49.

The heater applicator 49 consists of a matching network 60 and ystem of electrodes 46 and is located in the oven 44 which is a portion of the dielectric heater 38. The oven 44 which is 20 feet long, 13 feet wide and 10 feet high is constructed of 0.25-inch aluminum or steel plate and 10-gauge aluminum or steel sheet. The main body of the electrode system 46 is a 7-foot by 14-foot aluminum electrode whose height is adjustable from 28–40 inches by means of a reversible gear motor (not shown). The motor is operated by a three-position selector switch on an external control panel 50, which also displays electrode height. Heater elements 61 are mounted on the electrode 46 with a suitable RF pi-filter network (not shown) for decoupling the electrode heaters 61 from the rest of the RF circuit. The matching network 60 has a meter relay and amplifier (not shown) which, in combination with a motor-driven variable capacitor (not shown) automatically maintains power output at a preset level that is even throughout the oven 44. The coaxial cable 58 from the radiator source 56 connects to the matching network 60 which in turn feeds power into the electrode 46 to convert RF electricity into a RF magnetic field.

Processing Into Useful Materials

Figure 5:
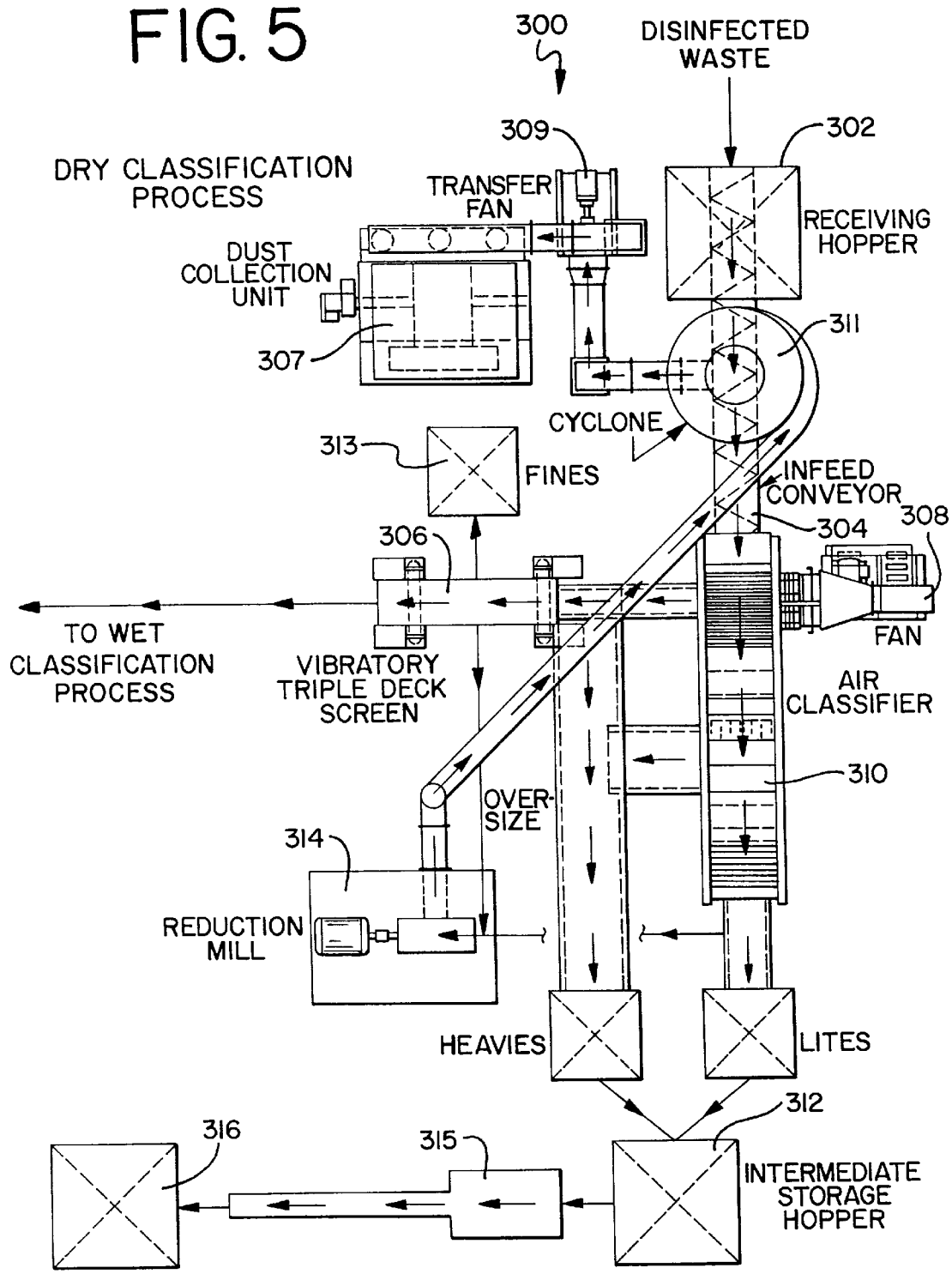
FIG. 5 schematically shows an embodiment of a refuse-derived fuel apparatus to be used with the apparatuses of FIGS. 1 and 2.

The disinfected waste of the embodiments of FIGS. 1 and 2 is next turned into useful materials such as refuse-derived fuel, or separated into useful components such as plastic. As shown in FIG. 5, the disinfected waste, after leaving the exit tunnel 42, is emptied from the heating containers 34, or alternatively is emptied from the exit end 241 of the fixed tube 240, into a dry waste classification system 300 such as the Steri-Fuel™ recovery system available from STERICYCLE, Inc. of Deerfield, Ill. Waste entering the dry waste classification system 300 is placed in a receiving hopper 302 and transported on an infeed conveyor 304 to a vibratory triple deck screen 306. Any dust in the waste moving on the infeed conveyor is drawn into a dust collection unit 307 by a dust transfer fan 309 via a cyclone 311 positioned over the infeed conveyor 304.

A fan 308 positioned adjacent an infeed conveyor 304 feeds an air classification system 310 which separates lightweight particulates from heavier dry waste material. These materials are both directed to intermediate storage hoppers. Remaining materials pass through a vibratory triple deck screen 306, which may be a layered screening device having three progressively finer mesh screens stacked in a spaced (coarsest mesh on top) relationship, filters out finely ground dry waste and directs the finely ground waste to a storage container 313. Larger dry waste is directed to a reduction mill 314 to further reduce the waste size. The reduced dry waste is air transported to the cyclone 311 and again processed through the system 300. The processed dry waste, after temporary storage in the intermediate storage hopper 312 is further processed to create bales or pellets of the processed dry waste.

The baler or pelletizer is a large compressing device 315 that compresses the wastes into a dense cube which can be secured by baling wires 66 or into small fuel pellets. These dense cubes or pellets of refuse-derived fuel leave the facility 12 and are transported to high-temperature burning devices such as cement kilns (not shown). In one embodiment, when the compressing means is a baler, a suitable baler may be 180 inches long, 50 inches wide and 76 inches high. It may be powered by a 15-horsepower electric motor (now shown) which can generate a "press weight" of 7,000 pounds. The baler is filled with disinfected waste fragments compressed to a dense cube measuring three feet by six feet by 2.5 feet. Each cube is secured by four thin baling wires 66. Each baled cube weighs approximately 1200 pounds. A forklift (not shown) loads baled cubes onto trucks for transport to regional cement kilns. In another embodiment, when the compressing device 315 is a pelletizer, a suitable pelletizer may be approximately 20 feet long by 4 feet wide by 4 feet high. Any of a number of standard electric motors may be used to drive a compressing mechanism capable of yielding compressed waste pellets having a diameter of 0.25 to 0.75 inch and a length of 0.5 to 1.0 inch. Various other pellet sizes and shapes are also suitable.

Laboratory analyses (Tables A, B, C and D) have shown that this processed medical waste, whether baled or pelletized, has a BTU value of approximately 12,016 per pound (Table A), comparing very favorably with the BTU value of coal, which ranges from about 11,000 to about 15,000 per pound. The sulfur content of the processed medical waste is less than 0.2% (Table A), and is lower than that of coal, which can vary from about 0.3% to about 4.0%.

Typical combustion characteristics for the medical waste are illustrated in Table D below.

TABLE A

RESULTS FROM BURNING PROCESSED MEDICAL WASTE
(Gabriel Laboratories, Inc.)

|  | As Received | Dry Basis |
| --- | --- | --- |
| Moisture (%) | 3.18 | — |
| Ash (%) | 2.78 | 2.87 |
| Volatiles (%) | 86.58 | 89.42 |
| Fixed Carbons (%) | 7.46 | 7.71 |
| TOTAL | 100.00 | 100.00 |
| Heat Production (BTU/lb) | 11,346 | 12,016 |
| Sulfur (%) | 0.11 | 0.11 |

TABLE B

MINERAL ANALYSIS OF PROCESSED MEDICAL WASTE ASH
(Gabriel Laboratories, Inc.)

| Mineral | Weight, Dry Basis (%) |
| --- | --- |
| Silica (SiO) | 24.61 |
| Alumina ($Al_2O_3$) | 12.49 |
| Titania ($TiO_2$) | 34.00 |
| Ferric Oxide ($Fe_2O_3$) | 7.69 |
| Lime (CaO) | 4.96 |
| Magnesia (MgO) | 1.23 |
| Potassium Oxide ($K_2O$) | 1.31 |
| Sodium Oxide ($Na_2O$) | 6.91 |
| Sulfur Trioxide ($SO_2$) | 7.81 |
| Phosphorus Pentoxide ($P_2O_5$) | 1.20 |
| Manganese Dioxide ($MnO_2$) | 0.08 |

TABLE C

LABORATORY ANALYSIS OF PROCESSED MEDICAL WASTE
(National Environmental Testing, Inc.)

| Ash (%) | 4.2 |
| --- | --- |
| Heat Production (BTU/lb) | 15,900 |
| Chlorine, Total (%) | <0.1 |
| Solids, Total (%) | 98.88 |
| Sulfur, Total (%) | 0.20 |
| Arsenic (ug/g ash) | <0.25 |
| Cadmium (ug/g ash) | <0.15 |
| Chromium, total (ug/g ash) | 2.6 |
| Lead (ug/g ash) | 3.6 |
| Mercury (ug/g ash) | 1.0 |
| Nickel (ug g ash) | 1.7 |
| Physical Characteristics | solid |
| Color | multicolored |
| Corrosivity (pH units) | 6.82 |

TABLE D

VOLATILE COMPOUNDS FROM INCINERATED BALED
MEDICAL WASTE (National Environmental Testing, Inc.)

| Compound | Content (ng/g) |
| --- | --- |
| Acrolein | <1000 |
| Acryonitrile | <1000 |
| Benzene | <100 |
| Bromodichloromethane | <100 |
| Bromoform | <100 |
| Bromomethane | <1000 |
| Carbon Tetrachloride | <100 |
| Chlorobenzene | <100 |

TABLE D-continued

VOLATILE COMPOUNDS FROM INCINERATED BALED MEDICAL WASTE (National Environmental Testing, Inc.)

| | |
|---|---|
| Chloroethane | <1000 |
| 2-Chloroethylvinyl ether | <100 |
| Chloroform | <100 |
| Chloromethane | <1000 |
| Dibromochloromethane | <100 |
| 1,2-Dichlorobenzene | <100 |
| 1,3-Dichlorobenzene | <100 |
| 1,4-Dichlorobenzene | <100 |
| 1,1-Dichloroethane | <100 |
| 1,2-Dichloroethane | <100 |
| cis-1,2-Dichloroethane | <100 |
| trans-1,2-Dichloroethane | <100 |
| 1,2-Dichloropropane | <100 |
| cis-1,3-Dichloropropane | <100 |
| trans-1,3-Dichloropropane | <100 |
| Ethyl benzene | <100 |
| Menthylene chloride | <100 |
| 1,1,2,2-Tetrachloroethane | <100 |
| Tetrachloroethane | <100 |
| Toluene | <100 |
| 1,1,1-Trichloroethane | <100 |
| 1,1,2-Trichloroethane | <100 |
| Trichloroethane | <100 |
| Trichlorofluoromethance | <100 |
| Vinyl chloride | <1000 |
| Xylenes, Total | <100 |
| PCB's | (ug/g) |
| PCB-1016 | <0.10 |
| PCB-1221 | <0.10 |
| PCB-1232 | <0.10 |
| PCB-1242 | <0.10 |
| PCB-1248 | <0.10 |
| PCB-1254 | <0.10 |
| PCB-1260 | <0.10 |

Plastics Reclamation

Another way disinfected medical waste fragments generated in the embodiments of FIGS. 1 and 2 can be transformed into useful material is through plastics reclamation. Plastics reclamation is preferably performed in a wet classification system 301 illustrated in FIG. 6 after the waste has passed through the dry classification system 300 described above with respect to FIG. 5. After having passed through the dry classification system, the waste stream mainly carries various types of plastic materials. The wet classification system further classifies types of plastics to filter out less useful plastics and retain the more valuable plastics for reclamation.

Figure 6:
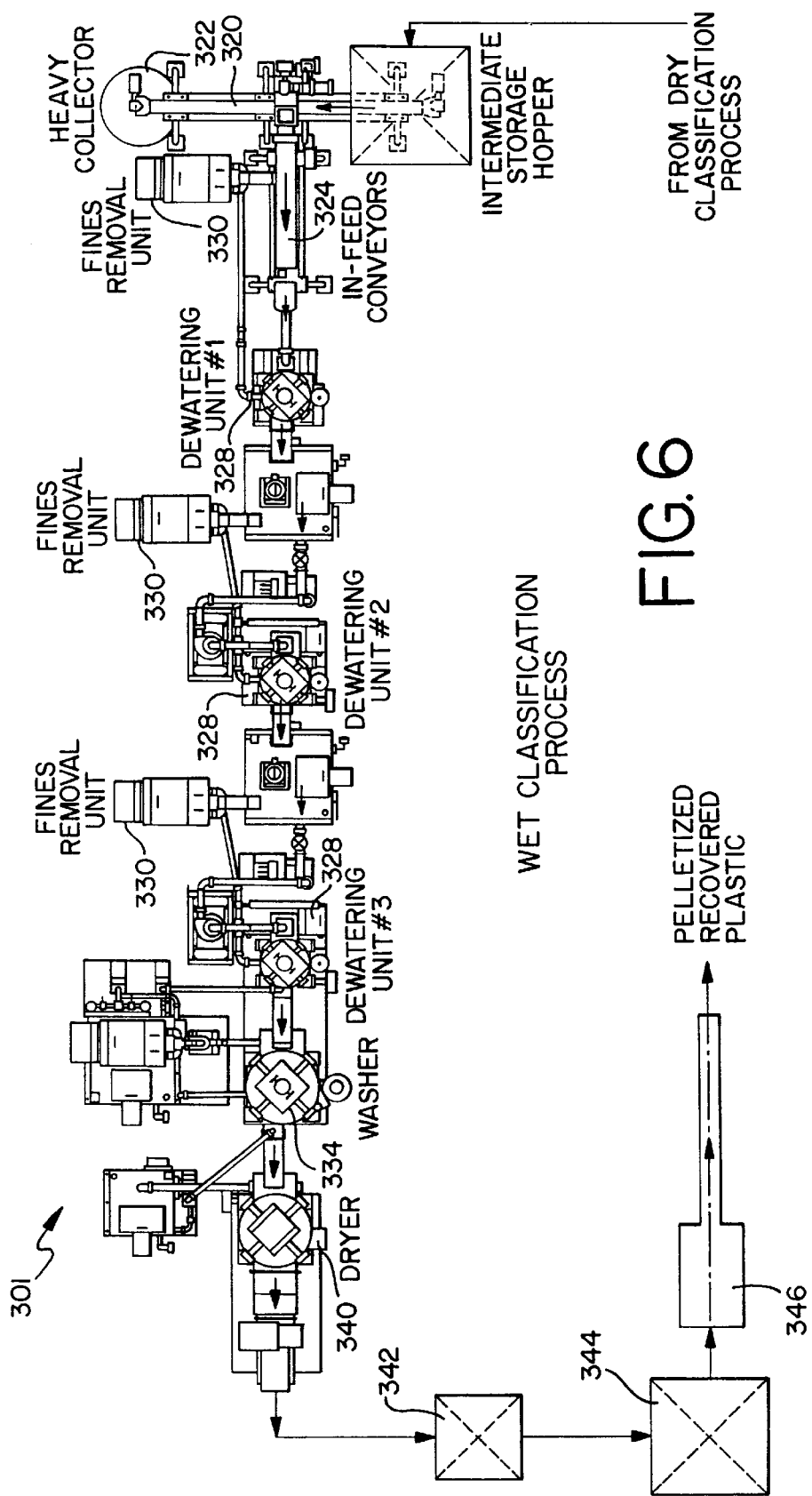
FIG. 6 schematically shows an embodiment of a plastics reclamation apparatus to be used with the apparatuses of FIGS. 1 and 2.

As shown in FIG. 6, a first conveyor 320 carries fragments from an intermediate hopper holding waste that has been processed through the dry classification system shown in FIG. 5 and residual high density material is filtered into a heavy collector bin 322. A second conveyor belt 324 carries the remaining fragments to the first of a series of de-watering units 328 and fine particle removal units 330. The de-watering units 328 each take the mainly plastic particles in the waste stream and classify the different types of plastic (and other materials) by their buoyancy in liquid. Fragments having a specific gravity falling within a predetermined range are sent on to the next de-watering unit 328. Fragments falling outside the predetermined range are either skimmed from the liquid and removed in a fines removal unit 330 or, for the denser materials, removed from the bottom of the de-watering unit. This separation process is highly effective in selecting for desired plastic such as polypropylene. The non-polypropylene materials removed in this process may be sent directly to a compressing device 346. The polypropylene emerging from this multi-stage wet classification system may be as much as 99.9% pure polypropylene and continues to be processed.

Once the polypropylene fragments pass through the final de-watering stage, they are hot washed in a washer 334 and processed through a dryer 340 which removes all moisture present on the fragments. The dried polypropylene flakes are then ready to be pelletized and made into such items as waste baskets, recycling bins and sharps disposal containers. Suitable plastics de-watering units, washers and driers can all be obtained from any of a number of commercial plastics recycling equipment manufacturers.

In one embodiment of the invention, the reclamation process stops after the hot washing step performed by the hot washer 334. At that point, the plastics are relatively devoid of non-plastic elements and can be dried and stored as flakes in a flake storage unit 342 for later resale. In another embodiment, the flakes are further processed by first transferring the flakes to a storage hopper 344 and then transferring the flakes to a compressing device such as a pelletizer 346.

The foregoing descriptions of the preferred embodiments of the present invention have been presented for purposes of illustration and description. They are not intended to be exhaustive or to limit the invention to the precise forms disclosed, and obviously many other modifications and variations are possible in light of the above teachings. The embodiments were chosen and described to best explain the principles of the invention and its practical applications, thereby enabling others skilled in the art to best utilize the invention in its various embodiments and with various modifications as are suited to the particular use contemplated. It is intended that the scope of the invention be defined by the following claims, including all equivalents.

EXAMPLES

Example 1

Mixed medical waste was shredded and compacted according to the first embodiment of the present invention and placed in 100 plastic containers made of polyethylene plastic, measuring 24 inches by 24 inches by 18 inches and weighing 50 pounds before filing. Each container was divided into four quadrants, into which temperature sensitive probes were placed. The temperature-sensitive tip of each probe was inserted to a depth of about two inches, which was considered the "coldest" spot in the waste container and least likely to reach the required temperature during passage through the dielectric heater. Then the covers were secured to the top of the containers. Each container was exposed to RF radiation in the frequency of 13 megahertz and an electric field strength of 50,000 volts per meter for approximately five minutes. The temperatures were recorded and tabulated as shown below:

| | |
|---|---|
| Mean Temperature | 94° C. |
| Standard Deviation. | 3.0° C. |
| Minimum Temperature | 91° C. |
| Maximum Temperature | 102° C. |
| Range | 11° C. |

| TEMPERATURE FREQUENCY DISTRIBUTION (° C.) | | |
|---|---|---|
| Range (° C.) | Count | Percent |
| From 85 up to 90 | 0 | 0 |
| From 90 up to 95 | 51 | 51 |
| From 95 up to 100 | 47 | 47 |
| From 100 up to 105 | 2 | 2 |

These statistics illustrate the evenness of the heating, in spite of the diverse nature of medical waste.

Example 2

Approximately 60 plastic containers were filled with about 200 pounds of medical waste that had been shredded and compacted according to the first embodiment of the present invention. The plastic containers were made of polyethylene plastic, measuring 24 inches by 24 inches by 18 inches and weighing 50 pounds before filling. Into each container at a depth of about two inches were placed test tubes containing viruses and controls. Temperature-sensitive indicators were attached to the top and bottom of each test tube. Then a cover was secured to each container. The viruses used for the study were Herpes simplex virus (HSV), type 2 (ATCC VR-540) and Poliovirus 3 (ATCC VR-193). To ensure a homogeneous and adequate supply of viruses for the study, stocks of HSV and poliovirus were grown prior to the initiation of the testing, harvested, frozen and validated according to standard methods. The medical waste containers were divided into eight treatment groups as shown below:

| Group | Time in Dielectric Heater (min) | Standing Time (min) |
|---|---|---|
| 1 | 4 | 0 |
| 2 | 4 | 20 |
| 3 | 10 | 0 |
| 4 | 10 | 20 |
| 5 | 6 | 0 |
| 6 | 6 | 20 |
| 7 | 8 | 0 |
| 8 | 8 | 20 |

Control test tubes of viruses were held at room temperature (about 25°C.) while the containers of medical waste with test viruses were subjected to sufficient RF radiation to bring the temperatures of the containers to approximately 60° C. Immediately after the standing period (additional time spent at room temperature), the containers were opened and the virus tubes removed and all tubes were sent to the microbiological laboratory. The temperature strips were removed and temperatures recorded. In all instances except three, the temperature exceeded 60° C.; and at least one of those failures appeared to be due to a malfunctioning temperature strip.

To determine the success of the disinfection, the viruses in the test tubes were first diluted multiple times. An aliquot from each of the dilutions was tested for its ability to still kill cells, according to standard methods. Only HSV and poliovirus from control tubes (which were not subject to dielectric heating) showed continued ability to kill cells, even when diluted by a factor of $10^5$. None of the HSV or poliovirus from heated tubes (Groups 1–8) showed any ability to kill cells, even when diluted only by a factor of 10.

Thus, the virus validation study demonstrated that the process of the first embodiment completely and uniformly destroys viruses even when the wastes are only heated to about 60°–70° C. and maintained at those temperatures for only about 10–30 minutes. Because the dielectric heater of the present invention heats medical waste to 90°–98° C., there is a large margin of safety for viral kill.

Example 3

Five medical waste containers each filled with about 200 pounds of medical waste fragments according to the method of the first embodiment of the present invention were selected and the covers were removed. Five strips of *Bacillus subtilis*, var. niger spores were deposited in each container. The spore strips were placed on top of the waste fragments, at the air-waste interface. This is the region of the waste container least likely to retain heat, because the heated waste gives up heat to the cooler air at this interface. Each sport strip contained about one million spores ($10^6$). *B. subtills* spores were chosen because they are highly resistant to heat treatment.

The covers were replaced on the medical waste containers and four of the five containers were run through the dielectric heater according to the method of the present invention. The fifth waste container did not pass through the dielectric heater and served as the control for the experiment. Each of the four containers passed through the 50,000 volt/m electric field. The dwell time, or time the containers spent in the electric field, was five minutes. The frequency of the radiowaves was 13 megahertz.

As soon as the containers left the dielectric heater, temperature probes were placed into the four quadrants of each waste container to record the initial temperatures, which were averaged. After standing for one hour at room temperature (about 25° C.), the first container was opened, the internal temperature was recorded and the spore strips were withdrawn. After standing for two hours at room temperature, the second container was opened, the internal temperature was recorded and the spore strips were withdrawn. The third and fourth containers were opened at three and four hours, respectively, and handled the same. According to standard method, the spores were diluted and cultured with the following results:

| | TEMPERATURE | | | |
|---|---|---|---|---|
| Standing Time (hours) | Initial (° C.) | Final (° C.) | Spore Concentration | Log Reduction |
| 1 | 98 | 92 | [11] $8.5 \times 10^2$ | 4 |
| 2 | 97 | 92 | $6.0 \times 10^2$ | 5 |
| 3 | 100 | 84 | $9.0 \times 10$ | 5 |
| 4 | 95 | 81 | $7.5 \times 10$ | 5 |
| Control | NA | NA | $1 \times 10^6$ | 0 |

This test proves that exposing the waste containers to RF radiation for five minutes is sufficient to produce a four log reduction with only one hour of standing time and five log reductions with longer standing times. In addition, as long as the containers stayed closed, the heavy, 50-pound containers lost only about 4°–8° C. per hour when the containers were in a 25° C. room. Because vegetative (non-spore) bacteria, yeasts and fungi are all less resistant to heat than are *B subtills* spores, these organisms would all be effectively eliminated by treatment according to the present invention.

I claim:

1. An apparatus for processing medical waste comprising:
   an extruder, the extruder configured to receive medical waste and continuously press the medical waste into a continuous tube of medical waste; and a source of electromagnetic radiation positioned outside of the continuous tube of medical waste, wherein the the source of electromagnetic radiation generates electromagnetic radiation that heats and disinfects the continuous tube to produce a disinfected continuous tube of medical waste.

2. The apparatus of claim 1, wherein the source of electromagnetic radiation primarily generates radio-frequency radiation.

3. An apparatus for processing medical waste comprising:

an extruder the extruder configured to receive medical waste and continuously press the medical waste;

a fixed tube, the fixed tube having a first end and a second end, the fixed tube having an expanding diameter wherein the diameter is greater at the second end than at the first end, and wherein the fixed tube is positioned to receive the medical waste from the extruder at the first end and form a continuous tube of medical waste; and a source of electromagnetic radiation positioned outside the fixed tube wherein the source of electromagnetic radiation is configured to generate electromagnetic radiation that heats and disinfects the continuous tube of medical waste to produce a disinfected continuous tube of medical waste.

4. The apparatus of claim 3, wherein the first end of the tube is located at an input of the electromagnetic source and the second end of the tube is located at an output of the electromagnetic source.

5. The apparatus of claim 3, wherein the first end has a diameter of twelve inches.

6. The apparatus of claim 3, wherein the diameter of the fixed tube increases one quarter inch for every one foot of distance from the first end of the fixed tube towards the second end of the tube.

7. The apparatus of claim 3, wherein a portion of the fixed tube is fixed within the source of electromagnetic radiation.

8. The apparatus of claim 7, wherein the portion fixed within the source of electromagnetic radiation is between the first and second ends of the fixed tube, whereby the extruder pushes the medical waste through the fixed tube and through the source of electromagnetic radiation.

9. The apparatus of claim 8, wherein the source of electromagnetic radiation primarily generates radio-frequency radiation.

10. The apparatus of claim 1, comprising a first conveyor to transport the medical waste to the extruder.

11. The apparatus of claim 3, further comprising a first conveyor device to transport the medical waste to a compacting device, wherein the compacting device compacts the medical waste to produce compacted medical waste.

12. The apparatus of claim 11, wherein the compacting device is coupled to the extruder, and wherein the continuous tube of medical waste comprises a continuous tube of compacted medical waste.

13. The apparatus of claim 11, wherein the fixed tube comprises a composite material.

14. The apparatus of claim 13, wherein the fixed tube of composite material is transparent to the electromagnetic radiation, whereby the compressed medical waste in the fixed tube receive substantially all radiation incident upon the fixed tube.

15. The apparatus of claim 14, wherein the electromagnetic radiation is primarily radio-frequency radiation.

16. The apparatus of claim 13, wherein the composite material comprises filament wound E-glass bedded in a fire resistant resin.

\* \* \* \* \*